US00PP35696P2

(12) United States Plant Patent
Huisman

(10) Patent No.: US PP35,696 P2
(45) Date of Patent: Mar. 12, 2024

(54) ***FATSIA* PLANT NAMED 'HBFP03'**

(50) Latin Name: *Fatsia polycarpa*
Varietal Denomination: HBFP03

(71) Applicant: Nico Huisman, Boskoop (NL)

(72) Inventor: Nico Huisman, Boskoop (NL)

(73) Assignee: HUISMAN BOOMKWEKERIJ B.V., Boskoop (NL)

( * ) Notice: Subject to any disclaimer, the term of this patent is extended or adjusted under 35 U.S.C. 154(b) by 0 days.

(21) Appl. No.: 18/218,047

(22) Filed: Jul. 4, 2023

(51) Int. Cl.
*A01H 6/00* (2018.01)
*A01H 5/00* (2018.01)

(52) U.S. Cl.
USPC ..... Plt./373

(58) Field of Classification Search
USPC ..... Plt./373
CPC ..... A01H 6/00; A01H 5/00
See application file for complete search history.

*Primary Examiner* — Keith O. Robinson
(74) *Attorney, Agent, or Firm* — Penny J. Aguirre

(57) ABSTRACT

A new cultivar of *Fatsia* plant named 'HBFP03' that is characterized by its large palmate leaves, its leaves that are deeply lobed with 7 to 9 lobes (occasionally 5 lobes on young leaves), its upper leaf surfaces that are matte to very slightly glossy.

2 Drawing Sheets

Botanical classification: *Fatsia polycarpa.*
Cultivar designation: 'HBFP03'.

BACKGROUND OF THE INVENTION

The present invention relates to a new and distinct cultivar of *Fatsia polycarpa* and will be referred to hereafter by its cultivar name, 'HBFP03'. 'HBFP03' is a new evergreen shrub grown for use as a landscape and container plant.

The new cultivar originated as a seedling that arose from seed planted from open pollination of an unnamed and unpatented plant of *Fatsia polycarpa*. The male parent is unknown but it is thought that *Fatsia polycarpa* 'Needham's Form' (not patented) is a probable parent based on its proximity to the female parent and the characteristics of the new cultivar.

Asexual propagation of the new cultivar was first accomplished under the direction of the Inventor by softwood cuttings in September of 2020 in Boskoop, The Netherlands. Asexual propagation of the new cultivar by softwood cuttings and tissue culture using meristematic tissue has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'HBFP03' as a new and unique cultivar of *Fatsia.*

1. 'HBFP03' exhibits large palmate leaves.
2. 'HBFP03' exhibits leaves that are deeply lobed with 7 to 9 lobes (occasionally lobes on young leaves).
3. 'HBFP03' exhibits upper leaf surfaces that are matte to very slightly glossy.

The female parent of 'HBFP03' differs from 'HBFP03' in having leaf surfaces that are moderately to highly glossy and leaf lobes that are narrower. The probable male parent of 'HBFP03' differs from 'HBFP03' in having leaf lobes that are narrower. 'HBFP03' can be most closely compared to the *Fatsia* cultivars 'Green Fingers' (not patented). 'Green Fingers' is similar to 'HBFP03' in overall plant habit and shape and leaves and in having large lobed leaves. 'Green Fingers' differs from 'HBFP03' in having leaf lobes that are narrower and leaf surfaces that are moderately glossy.

BRIEF DESCRIPTION OF THE DRAWINGS

The accompanying color photographs illustrate the overall appearance and distinct characteristics of the new *Fatsia*. The photographs were taken of a plant 2.5 years in age of the new cultivar as grown in a conventional greenhouse in 19-cm containers in Boskoop, The Netherlands.

The photograph in FIG. 1 provides a side view of the plant of 'HBFP03'.

Figure 1:
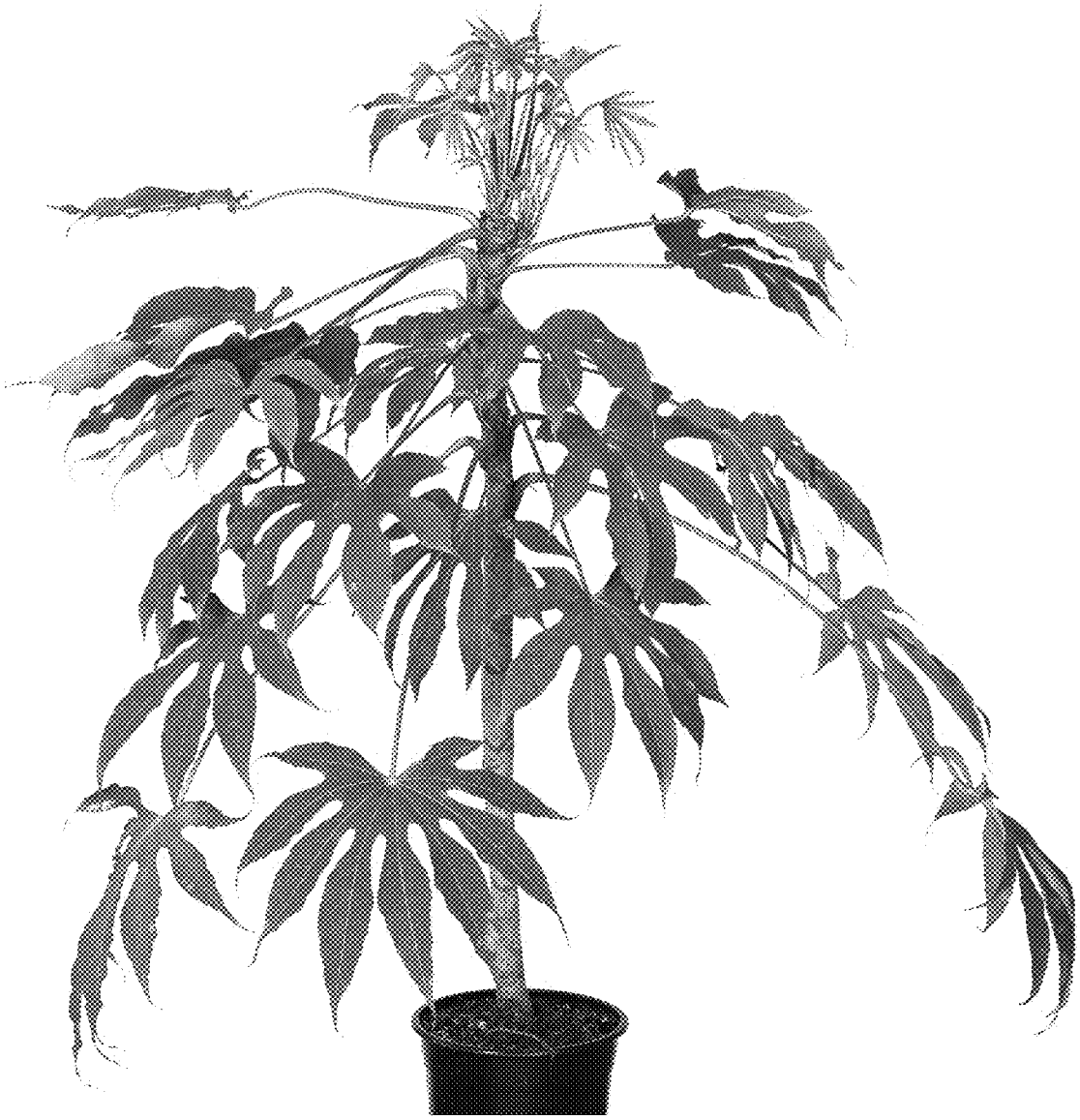
Figure 2:
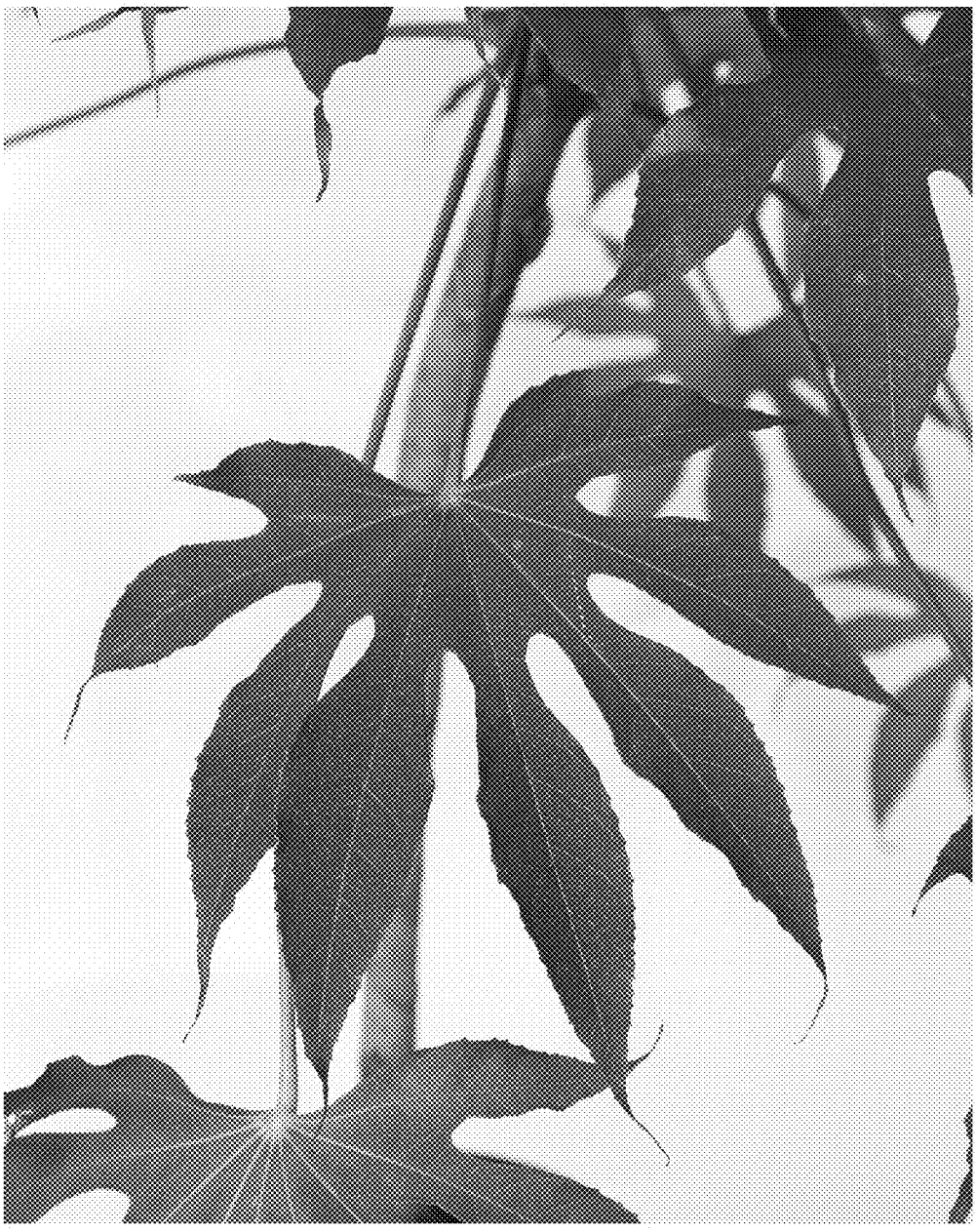

The photograph in FIG. 2 provides a close-up view of the foliage of 'HBFP03'.

The colors in the photographs are as close as possible with the digital photography techniques available, the color values cited in the detailed botanical description accurately describe the colors of the new *Fatsia.*

DETAILED BOTANICAL DESCRIPTION OF THE PLANT

The following is a detailed description of 2.5 year-old plants of the new cultivar as grown in a conventional greenhouse in 19-cm containers in Boskoop, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Plant type.*—Evergreen shrub.

*Plant habit*.—Broadly upright with inflorescences held above the foliage.

*Height and spread*.—An average of 95 cm in height and 91 cm in diameter.

*Cold hardiness*.—At least in U.S.D.A. Zone 8.

*Diseases and pests*.—No susceptibility or resistance to diseases or pests has been observed.

*Root description*.—Fibrous.

*Propagation*.—Softwood cuttings and tissue culture using meristematic tissue.

*Root development*.—An average of 6 weeks for root initiation and 8 months to produce a rooted cutting.

*Growth rate*.—Young plants vigorous, older plants moderate.

Branch description:

*Branch shape*.—Round.

*Branch size*.—Average of 78 cm in length, 2.5 cm in diameter.

*Branch surface*.—Matte, young and mature stems densely covered with a stellate indumentum, a blend of N200B and 201A in color.

*Branch color*.—Young; 148A, mature; 137C, older stems and bark; 197B to 197D.

*Branch strength*.—Strong.

*Branch aspect*.—Main; average angle of 90°, lateral; average angle of 40° to main branch.

*Internode length*.—An average of 1.6 cm.

*Branching*.—1 main branch, 2 lateral branches.

Foliage description:

*Leaf shape*.—Palmately cleft to parted, orbicular to nearly reniform in outline.

*Leaf division*.—Simple.

*Leaf base*.—Broad, hastate, basal lobes free.

*Leaf apex*.—Long, narrow apiculate.

*Leaf fragrance*.—None.

*Leaf venation*.—Palmate, upper surface color; 143A, lower surface color; 144C.

*Leaf quantity*.—An average of 25 per lateral branch.

*Leaf margins*.—Coarsely dentate to serrate, moderately undulate.

*Leaf lobes*.—Average of 7 to 9 lobes, occasionally 5 lobes in young leaves, deep sinuses, convergent to parallel.

*Leaf arrangement*.—Alternate.

*Leaf aspect*.—Slightly convex.

*Leaf attachment*.—Petiolate.

*Leaf surface*.—Upper surface glabrous, matte to very slightly glossy, lower surface very slightly glossy, very sparsely pubescent with stellate hairs, sparsely on the main veins, 199A in color.

*Leaf size*.—Average of 27.2 cm in length and 29.7 cm width.

*Leaf color*.—Young leaves upper surface; a blend of 144A and N144B, young leaves lower surface; a blend of 144B, N144B, main veins 146C, mature leaves upper surface; NN137A and NN137B, mature lower surface; 147B.

*Petioles*.—Average of 40.7 cm in length and 4 mm in diameter, strong, color; upper surface 137B, lower surface 144A, flushed with 137B, held in an average angle of 90°, both surfaces slightly glossy and very sparsely pubescent with stellate hairs, distal end moderately pubescent, pubescence 199A in color, corky ribs present; at proximal end on upper surface 1 cm in length, 6 mm in width, at distal end on lower surface 6 mm in length, 0.5 mm in width, both are 199B and 199C in color.

*Stipules*.—None.

Inflorescence description: None observed to date.

Fruit and seed: None observed to date.

It is claimed:

1. A new and distinct cultivar of *Fatsia* plant named 'HBFP03' as herein illustrated and described.

* * * * *